United States Patent [19]

Wagner

[11] Patent Number: 4,573,970
[45] Date of Patent: Mar. 4, 1986

[54] SUCTION INJECTOR

[76] Inventor: Wolfgang Wagner, Exerzierstr. 1, Berlin 65, Fed. Rep. of Germany

[21] Appl. No.: 405,560

[22] Filed: Aug. 6, 1982

Related U.S. Application Data

[60] Continuation-in-part of Ser. No. 241,378, Feb. 26, 1981, Pat. No. 4,393,870, which is a continuation-in-part of Ser. No. 93,615, Nov. 9, 1979, Pat. No. 4,284,077, which is a division of Ser. No. 933,136, Aug. 14, 1978, abandoned, and a continuation-in-part of Ser. No. 793,951, May 5, 1977, Pat. No. 4,114,691, which is a continuation-in-part of Ser. No. 634,741, Nov. 21, 1975, abandoned.

[51] Int. Cl.$^4$ .............................................. A61M 5/32
[52] U.S. Cl. .................................................... 604/115
[58] Field of Search ................. 604/115, 93, 117, 118, 604/119, 245-247

[56] References Cited

U.S. PATENT DOCUMENTS

2,743,723  5/1956  Hein ..................................... 604/115
4,299,219  11/1981  Norris, Jr. ............................ 604/115

Primary Examiner—John D. Yasko
Attorney, Agent, or Firm—Ralf H. Siegemund

[57] ABSTRACT

An automatic injection apparatus has a tubular housing formed with a cylindrical boring and with a suction cup to receive a syringe with canula surrounding said cannula. The upper end of said housing is covered by a pot cylinder provided with an inlet bore for the air, having a cover with a sealing ring towards said tubular housing, fixing brackets to secure the sealing; supporting rings for the attachment of said syringe; while the piston rod is held in the central part of a folding bellows sealed to said cover. A parallel covering tube connected with said tubular housing by a base plate which contains a cross over duct between said boring of said tubular housing and a suction producing folded bellows sealed to said base plate and to a sleeve sealed to a lid plate, said shell sliding on a central bar, said sliding movement restricted by a cross pin lead by a longitudinal slot of said shell, which is surrounded by a pressure spring for extension of said folded bellows with said shell. This extension movement is blocked by a rod connected with said lid plate sliding in a guiding tube, caught in a notching groove by a catch pin, until an annular groove of a releasing bar, when lifted by the raising of a shell, surrounding the suction cup, frees the movement of catch pin and also said folding bellows, which produces suction, working through said cross over duct, so that the skin, closing the rim of said suction cup, is raised and delayed by the friction between the syringe piston and syringe cylinder. The little folding bellows collapses and presses the liquid medicine from the syringe through the cannula under the skin, elevated by suction. A nozzle, limiting a reventilation tube, effects the reventilation of the suction cup. A bush, connected with said pot cylinder, is shiftable along said rod and allows the removal of said pot cylinder from the tubular housing for a replacement of the syringe.

22 Claims, 14 Drawing Figures

SUCTION INJECTOR

CROSS-REFERENCE TO RELATED APPLICATIONS

This application is a continuation-in-part of my copending patent application Ser. No. 241,378, filed Feb. 26, 1981, now U.S. Pat. No. 4,393,870 which is a continuation-in-part of my copending patent application Ser. No. 093,615, filed Nov. 9, 1979 now U.S. Pat. No. 4,284,077 which is a divisional application under 37 CFR 1.60 of prior patent application Ser. No. 933,136, filed Aug. 14, 1978 which is now abandoned and is in turn a continuation-in-part of the patent application Ser. No. 793,951, filed May 5, 1977, now U.S. Pat. No. 4,114,691 which in turn is a continuation-in-part of my application Ser. No. 634,741, filed Nov. 21, 1975, now abandoned, and the entire disclosure of which is herewith incorporated by reference. This application is also related to my copending patent applications Ser. No. 618,686, filed Dec. 21, 1975, Ser. No. 634,742, filed Nov. 21, 1975, and Ser. No. 639,685, filed Dec. 8, 1975, all of whose disclosures are also herewith incorporated by reference.

BACKGROUND OF THE INVENTION

The invention relates generally to medical technology, and more particularly, it relates to injection therapy. Devices, which drive injection cannula into the body by first sucking the skin into the cannula tip are known from prior art. With the suction injection, only the upper layers of the skin are penetrated by the cannula tip, and the greater vessels, nerves and bone are not reached, which avoids pain and dangerous injection into blood vessels. The finest vessels in fatty tissue can be penetrated by the cannula tip. These vessels can be hurt by liquid pressure. In particular, the injection of christalline heparine, insulin or allergene can trigger dangerous conditions of shock. There are even injectors on the market, which permit the patient to alter the depth, which the needle, driven by spring pressure, will penetrate the tissue before the contents of the syringe are emptied under considerable pressure, although the patient himself cannot be the proper judge of this. The usual suction movement of the syringe piston to the end of the cannula within the container does not in this case take place. In one of these injectors, a transparent water-like cold-sterilizer is used for the constant cleansing of the dose pump within the injector. This fluid can easily be mistaken for insulin. Only the fact, that it is difficult and unpleasant to use, has prevented fatalities up til now. If suction injection makes the suction movement of a syringe unnecessary, this raises the question, why, in view of the possibility of dosing from large supply bottles, research on injectors which use disposable syringes is of use. It is useful, in particular, because, especially in doctors' practices and clinics, there is always danger of contagion, particularly of hepatitis, even if there is only a brief and limited contact to the medicine supply, and because there will be interruptions in use.

The only suction injector for use on humans, which is known to the inventor, is not suitable for one-handed use, because negative pressure is caused by the movement of the piston. It was never put on the market for that reason, because the extent of the body surface, which can be used for injection, and the careful treatment of tissue are among the most important priorities for the invention.

SUMMARY OF THE INVENTION

It is therefore an object of the invention to overcome the disadvantage of the prior art injections and especially of suction injectors.

Another object of the invention is a suction injector which may be easily released from the human skin after injection.

Still another object of the invention is to provide a suction injector in which the syringes can be easily changed.

A further object of the invention is to simplify or eliminate the complicated and expensive switch mechanisms which have been necessary to insure that the injection only takes place after the skin has been sucked into the cannula.

This and other objects of the invention are attained by a suction injector particularly for use with hypodermic injections, comprised of a tubular housing, a partition, arranged in a sealed manner to said housing, for movement in said housing, a supporting case for a container filled with a liquid medicine, operated in diminution of said container by said movement through a canula operatively connected to said container and partially surrounded by the end of said tubular housing, serving as a suction cup, and a suction hose leading from the tubular housing to a vacuum source, the influence of this causing, when said end of the tubular housing is closed, the skin to rise onto the cannula tip and, delayed by friction between the moving parts, to expel the liquid medicine of said container.

A piston or a folding bellows or an elastic ball may be used as a partition between the outer air and the interior of the tubular housing. The syringe, which is prepared for injection in the standard manner, can be fastened to that piston or can be in a supporting case, which also serves to reduce the empty space within the tubular housing and thus, in addition, to reduce the suction volume. Intramuscular injections can be given without maintenance of distance between the syringe walls and the skin. The attachment to the piston can be done with clamps and facilitated by a spring biased pressing plate attached to said piston. The supporting case may be firmly embedded in the tubular housing, which means that the syringe must enter from above, if that part of the suction cup is not removable. This part can be stuck onto the tubular housing from the outside as a socket or sealed to it from the inside, which takes into account the fact, that the suction cup can as a rule be made smaller than the diameter of the syringe. The emptying syringe flange, which is a handicap for suction injection because of the increase in empty space, is well suited for locking in a supporting case through turning over an oval plate passage. A division between the tubular housing and the suction cup can be avoided, if the syringe is inserted from above. Because of the danger of contact between the cannula and the case, it is better, if the sealing piston is lowered to the suction cup. The attaching mechanism for the syringe is best attached to the smaller and often round endplate of the syringe piston, which however requires a considerable friction power between the syringe cylinder and the piston, in order to avoid accidental intake of air or emptying of the syringe. Even springs with folding bellows should have considerable piston friction, while the folding bellows itself eliminates some loss of friction. This does not apply to precision sealing pistons, which are however too expensive. Mechanisms of the piston-type have not up til now proved useful despite their simple construction, because sealing requires maintenance, and because even the smallest grains of sand, sucked in from the pores of the skin, have led to small cracks in the cylinder wall, which rapidly hampered proper functioning. Better material causes higher costs. For this reason, a folding bellows was used as vacuum generator (or better vacuum source). To save space, the folding bellows has a spring inside of itself and a tubular passage, which itself adds to the extent of the suction creating space by lifting a kind of piston rod. The upwards movement of the suction creating folding bellows presents a source of danger for the eyes of the user. This danger is increased, when, by accident, this movement is triggered, before a tight contact between that suction cup and the skin has been established, this being necessary to limit the movement of the bellows. For this reason, it is necessary that the suction creating procedure is made only possible, after a blocking protective plate has been pulled out far enough to hold the face of the user at a sufficient distance. This is brought about by a catching mechanism between the releasing bar and blocking rod, to which the protective plate is fastened, and the rod, which holds the folding bellows. The small folding bellows, which brings about the lowering of the syringe piston and contains on its lower side the supporting case for the syringe fastening, can be pushed along this rod over a bushing to the large folding bellows and swung out for syringe changes. A leaf spring plate serves as the joint. The triggering at the moment of contact with the skin, which reduces the necessity for a decision by the patient and ensures the proper timing for the creation of suction, is brought about by means of a shell, which surrounds the suction cup, and which is pressed down by a bias spring, which lies on a ledge, the sharp rim of which, in the event of uneven pressure, which can be caused by false positioning on the skin, touches the tubular housing and blocks the pushing and triggering movement. Placing the bolts between the tubular housing and said shell in large round holes was determined to be the cheapest and most practical solution, since this brings about a stabilization of the position of the shell in rest position. This is immediately changed, when the bolts are lifted into the round holes. A vacuum leak through a valve or half-permeable membrane eliminates the necessity of expensive and delicate mechanical reventilation devices. The triggering of a rest lever for the suction producing piston can bring about reventilation for the simple solution using two parallel piston-cylinder-pumps. The suction is at first stored because of a hose clip, after being produced by piston movement, and then causes by opening the valve an effect on skin and piston of the tubular housing and thus the injection. A simple plunger, on the alternate sides of both pistons and removable for use, helps to save space. A jet pump can, of course, also be used as a vacuum source. Water jet pumps have been used for years for this purpose in doctors' laboratories because of their high capacity. A jet pump, driven by a carbon dioxide cartridge, can, of course, also be used, or simply sucking on the mouthpiece, even though the relation between the maximal capacity of the chest and its remaining volume is not optimal. A disposable bag cannula with or without attachment to its supporting case is useful after the removal of a covering shell.

DETAILED DESCRIPTION OF THE PREFERRED EMBODIMENTS

Figure 1:
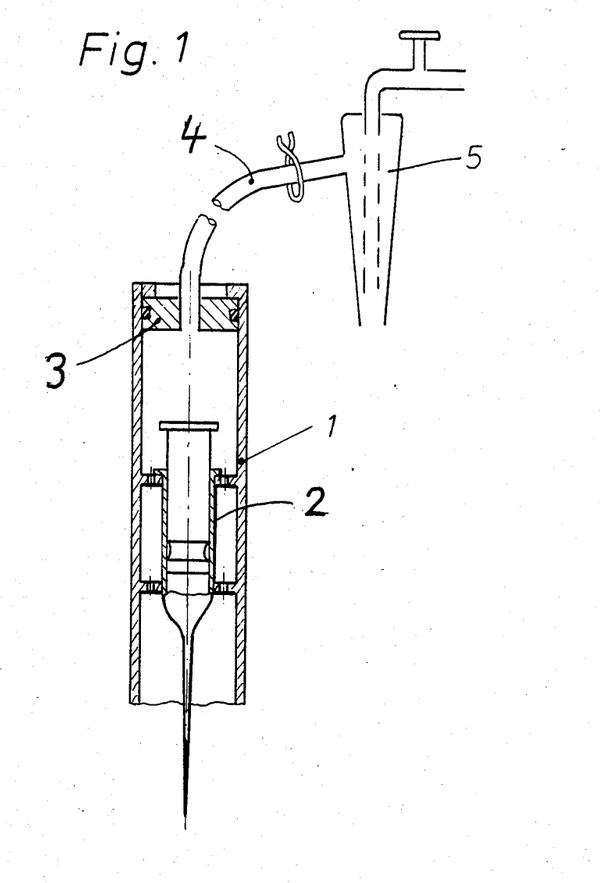
FIG. 1 shows in sectional side view the largest part of an embodiment of the invention in connection with a water stream pump as a vacuum source and a piston as partition between the suction area over the skin within the tubular housing and the exterior air.

FIG. 1 shows the first example of the invention in a vertical section in a partial view. The lower part of the tubular housing (1) is omitted. The syringe is positioned with this supporting case flange in an upper distance ring with holes and supported by a second distance ring with holes together in a supporting case (2). The piston (3), sealed towards the tubular housing wall, has a centrical suction hose (4), which leads to a water stream pump (5). If the under part of the tubular housing (1) is positioned on the skin, the pressure into the housing increases and the skin will be sucked on into the cannula, and the friction of the piston may overcome the friction between the piston and the housing wall and move the piston downwards toward the syringe piston, pushing them, until their contents are emptied.

Figure 2:
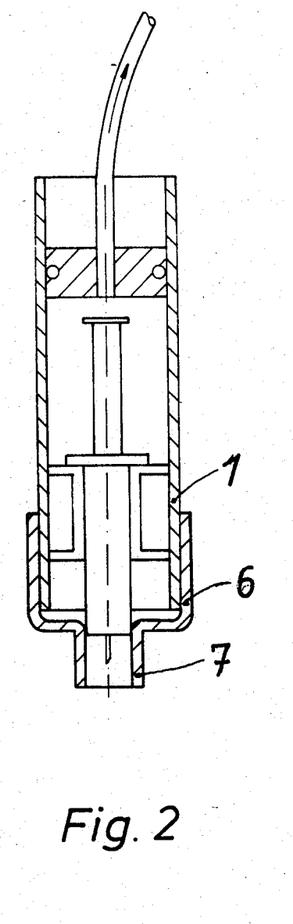
FIG. 2 is a sectionl side view of an embodiment of the invention in FIG. 1, which was supplemented and slightly modified.

FIG. 2 shows a device, identical with that of FIG. 1 except that the lower section is shown and varied by a socket (6), which narrows downwards to a suction cup (7), which sticks tightly to the tubular housing (1).

Figure 3:
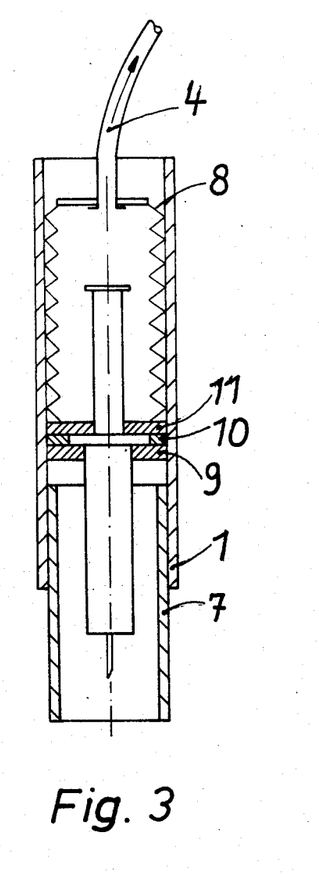
FIG. 3 is a sectional side view of an embodiment of the invention as in FIG. 1, where the suction cup is placed on a folded bellows to serve as a partition, and where the supporting case is modified.

In FIG. 3, the piston (3) is replaced by a folding bellows (8), which is tightly fastened to a lock for the syringe flange, consisting of a lower disc with an oval centrical hole (9), a wider distance ring (10) and an upper aperture disc (11). The syringe flange may be pushed forward through the oval hole of the lower disc, and then the syringe turned perhaps ninety degrees, in this way locking between said lower disc and the upper aperture disc. The shell serving as suction cup (7) may be inserted into the tubular housing (1), the outer side of the former being then within the latter. Under the influence of an underpressure source working through the suction hose (4), the skin may be sucked into the suction cup, and then the folding bellows may be lowered, and the syringe emptied.

Figure 4:
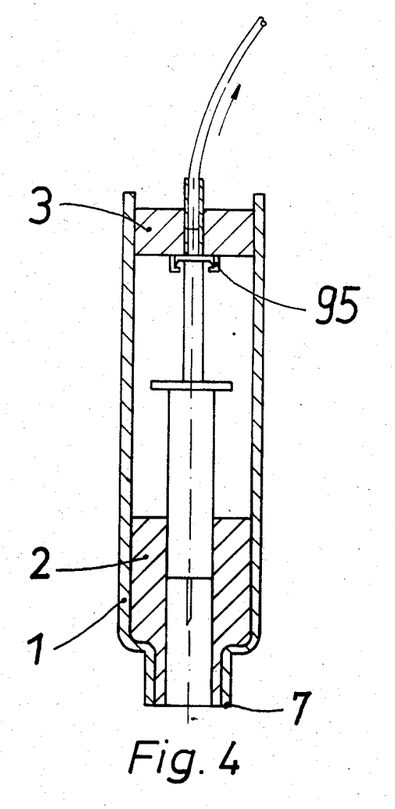
FIG. 4 shows a sectional side view of an embodiment of the invention, as in FIG. 1, with an attachment of the syringe to said piston and a modification of the suction cup and the supporting case.

In the example of FIG. 4, which otherwise corresponds closely to the example of FIG. 1, the lower part of the tubular housing (1) is connected to the suction cup (7), and the supporting case (2), which holds the syringe in a perpendicular position in the middle and prevents a too deep lowering of the syringe cylinder against the skin by means of the syringe flange, is given a corresponding form. The end plate of the syringe piston is fastened in a holding rail (95) on the piston (3).

Figure 5:
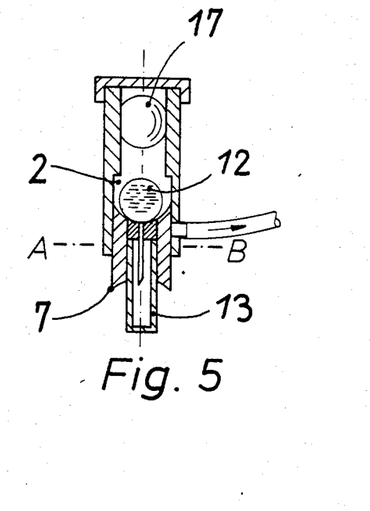
FIG. 5 shows a sectional side view of an embodiment of the invention as in FIG. 1, in which the syringe is replaced by a bag cannula, and suction is brought about by means of a mouthpiece.

FIG. 5 shows a device, in which the syringe is replaced by a bag cannula (12) and the piston (3) by an elastic ball (17). The supporting case (2) has beneath it a cavity for the cannula bag, which can also be attached here. The lower cavity is formed by the suction cup (7). The supporting case and the bag cannula are pushed on the covering shell (13) into the tubular housing.

Figure 6:
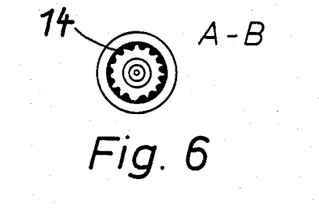
FIG. 6 is a cross-section of the device shown in FIG. 5. The section at the height A-B is shown after the removal of the protective lid.

FIG. 6 shows a cross-section through the device of FIG. 5 at the level of the line A-B. The channels (14) in the surface of the supporting case, through which air can flow upwards from the suction cup area, are illustrated. The suction cup rim is formed by the housing.

Figure 7:
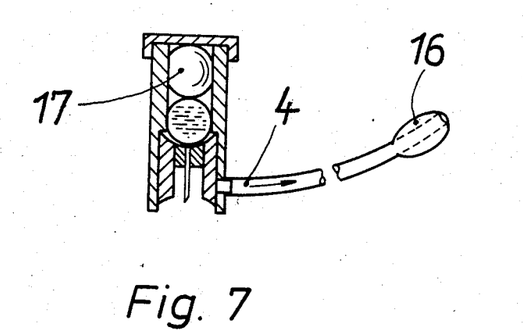
FIG. 7 shows the device in sectional side view of FIG. 5, after the bag cannula has been pushed into the tubular housing.

FIG. 7 shows the device of FIG. 5 right before use. The protective lid (15) still has to be taken off; the covering shell has already been removed. The suction hose (4) leads to a mouthpiece (16), which suction acts to lower the ball (17) and to cause the emptying of the cannula bag, after the skin has been raised.

Figure 8:
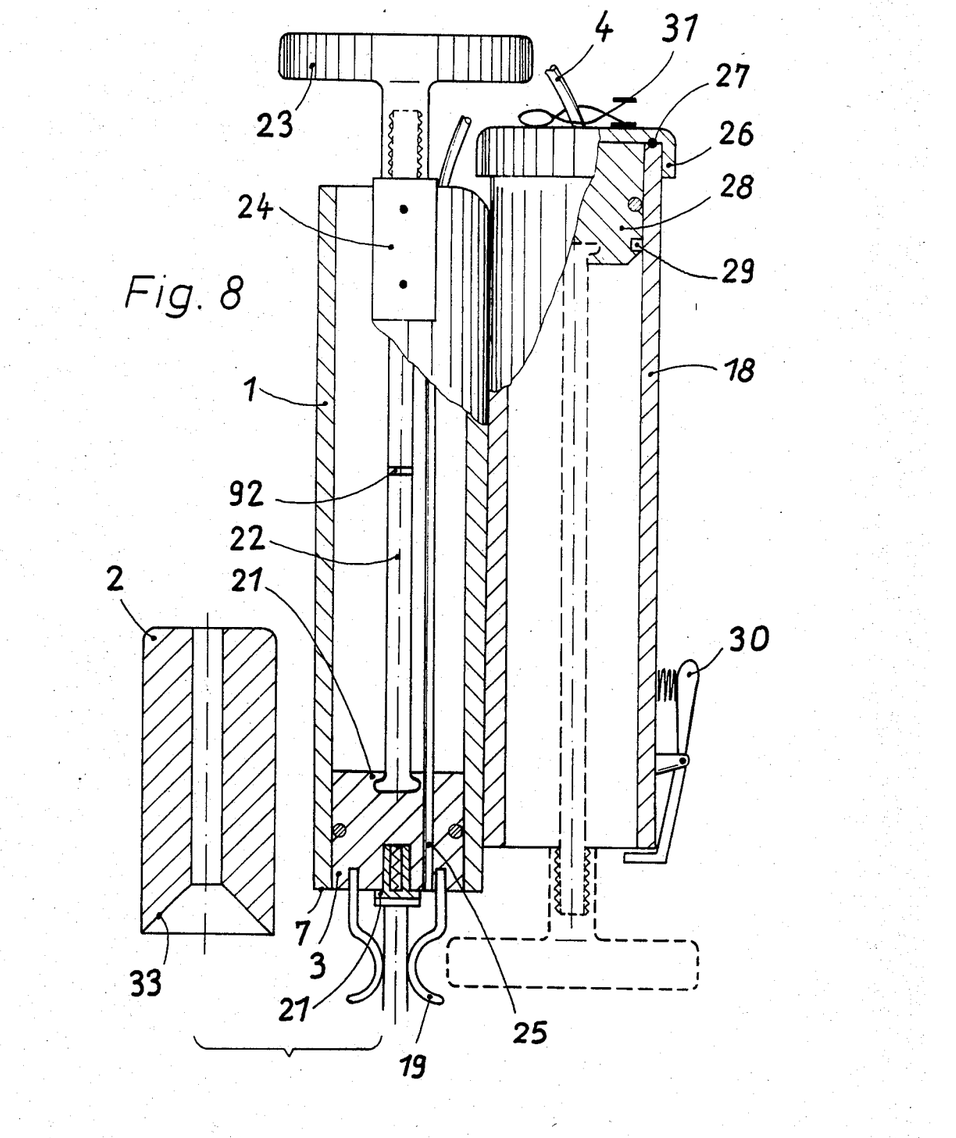
FIG. 8 shows in sectional side view an embodiment of the invention, in which a plunger pump is the vacuum source, which is operated by hand.

FIG. 8 shows an example, in which a parallel tube (18), which serves as a plunger-pump-cylinder, is attached to the tubular housing (1), in such a way that the end of the tubular housing, which is formed by the suction cup (7), is pushed downwards over the end of the tube (18). The piston (3) in the tubular housing extends beyond the suction cup rim and has here spring clips (19) for pushing in the end plate of the syringe piston. In a central blind hole of the piston, there is a springbiased peg (20), the end plate of which is pressed against the end plate of the syringe piston, and the position of which is kept vertical. Towards the inside of the cylinder, there is the central boring for a bayonet cap catch (21), in which the rod (22) with its bayonet cap on the end and with the handgrip (23) is screwed. A handle-like angle-plate (24) has a boring for the penetration of the rod. The suction hose (4) leads through an eccentric boring (25) in the piston (3) through a loop in the sealed central boring of the screw lid (26) with the sealing ring (27). The pump plunger (28) has beneath it a bayonet cap catch, into which is indicated by the broken lines, the piston rod (22) can be screwed, so that the pump plunger can be drawn out, until the ring groove (29) is blocked by the blocking lever (30) on springs. The hose clip (31), which is fastened to the screw lid (26), prevents air from entering the space between that suction cup and the piston (3). For use, the syringe piston is first raised until it reaches the angle plate (24), after it has been pushed into the spring clips (19) by pulling on the hand grip (23). Then the supporting case (2) is pushed into the tubular housing (1), so that its cavity (33) faces downwards. The piston rod is now removed from the piston (3) and is screwed into the pump plunger (28) and pulled, until it snaps into the blocking lever (30). Now the piston rod is removed from the pump plunger (28), and the suction cup is placed on the skin, and then, by means of pressure on the tube clamp (31), the flow of air is released into the tube (18); the skin is first drawn into the cannula of the syringe, which is then emptied. The triggering of the blocking lever causes the sealing piston to spring back thus reventilating the suction cup. A marking (92) on the piston rod indicates how far the pump plunger (28) has to be lowered into the pump barrel, in order to create sufficient suction even when little force is used.

Figure 9:
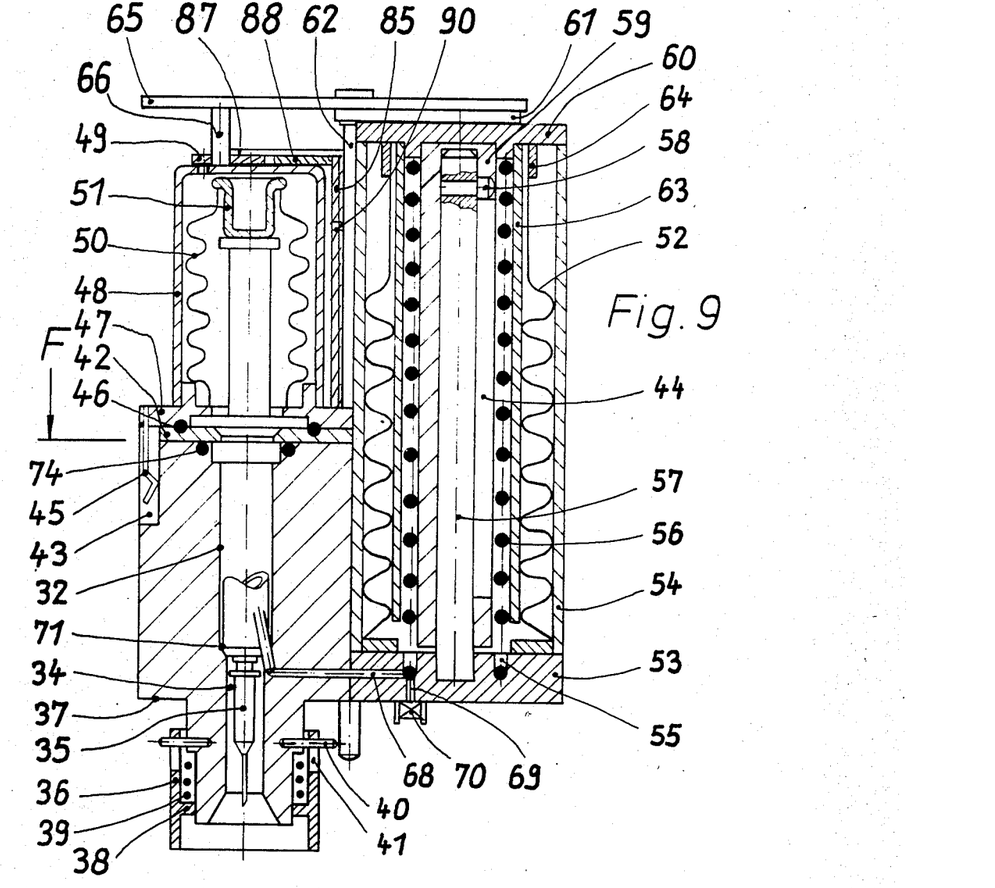
FIG. 9 is a sectional side view of an embodiment of the invention, in which the vacuum source is a folding bellows, which is extended by stored spring power.

FIG. 9 is a cross-section of an example similar to FIG. 4, in which, however, instead of two pistons two folding bellows are used. The device consists of a tubular housing (1) with a central boring (32), into which fits a syringe cylinder, and which narrows as it extends downward into the boring (34), which surrounds the syringe cone and the cannula which is attached to it, and which opens downwards into the suction cup (7).

The tubular housing (1) has on its lower exterior also a change in caliber, so that it has a shoulder towards towards the shell (36), which surrounds the suction cup. The shell can be pushed upwards and has towards the tubular housing a gliding sharp-edged ring (38), upon which the pressure spring (39) is positioned also touching the shoulder (37) of the tubular housing (1). The shell (36) is prevented by two facing bolts (40) from falling downwards, because they go through corresponding holes in the shell (36) to be firmly embedded in the narrower part of the tubular housing (1). The cover (42) on the tubular housing (1) has three baffles (94), which reach into the three locking grooves (43) of the tubular housing (1). By means of the baffles, the fixing brackets (45) gain grip and press the sealing ring (46) under the holding ring (47), from which the fixing brackets (45) originate, against the cover (42). The pot (48) with the ventilating boring (49), which can be removed from the tubular housing (1), firmly enters into the holding ring. In the center of the holding ring (47) there is a plate with a central oval hole for the syringe cylinder flange to fit into. Over this there is a distance ring of large diameter, and on this there is a round hole disc as passage for the syringe piston. The folding bellows (50) is tightly sealed to the cylinder (51). The suction creating folding bellows (52) is sealed onto a base plate (53), which procedes from the tubular housing (1). The protective tube (54) is attached to this base plate (53). A pressure spring (56) lies inwards from the folding bellows (52) within a groove (55). There is a central rod (57) firmly embedded in a hole in the center of the base plate (53). This has a cross-pin (58) close to its upper end. This rod grips into a longitudinal slit (44) of the movable tube (59), which glides along the central rod (57), and thus limits the movement of the tube. The tube (59) fits into the lid plate (60), which itself is attached to the connecting plate (61). The connecting plate is itself connected to the rod (62) through a boring The sleeve (63) is also tightly connected with the lid plate (60). The upper end of the folding bellows (52) is tightly connected with the sleeve (63) by means of a flange (64). A protective plate (65) with forked continuations is connected by means of the two blocking rods (66, 67) with the tubular housing. The blocking rods (66,67) can be pushed along two longitudinal borings on the tubular housing (1). Between the groove (55) in the base plate (53) and the boring (34) around the cannula, there is a cross-over duct (68). The boring (69) for reventilation contains a nozzle (70). The blind boring (71) facilitates the entrance of air between the suction cup and the folding bellows.

Figure 10:
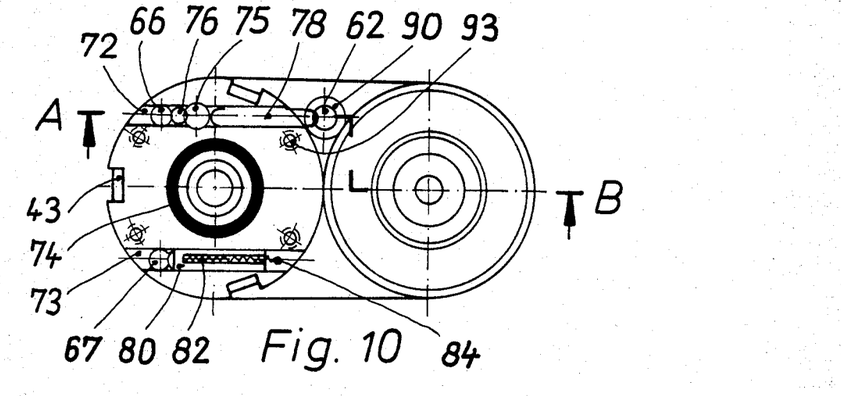
FIG. 10 is an embodiment of the device in FIG. 9 in cross-section, seen from above at the level A-B of FIG. 9.

FIG. 10 shows a view from above at the level of view F of the cover (42), in which it can be seen, that the cover has half-moon-shaped continuations, which support the protective tube (54) and give the leading tube (90) grip on the rod (62). The cover (42) on the tubular housing (1) covers two parallel angular grooves (72,73) on said tubular housing and is provided with a sealing ring (74) to seal it to the syringe cylinder. Four attaching screws (93) guarantee equally distributed pressure on the cover (42) and the sealing ring (74). The releasing bar (75) lies in the longitudinal boring of the tubular housing (1) along which it can be pushed. Between the releasing bar (75) and the blocking rod (66) in the angular groove (72) lies the ball (76), which with a cap grips into the notch of the annular groove (77, see FIG. 11) of the releasing bar (75) and blocks it, while the catch pin (78), rising above the groove grips into the notch (79) of the rod (62) through a boring in the leading tube (90) and limits its motion. In the angular groove (73) lies the square (80), the sharp lower edge of which touches the edge of a notch of the blocking rod (67) and prevents said blocking rod from being moved upwards out of the tubular housing (1). For this function there is a pressure spring (82), which supports itself on the screw (84), in a blind boring of the square (80).

Figure 11:
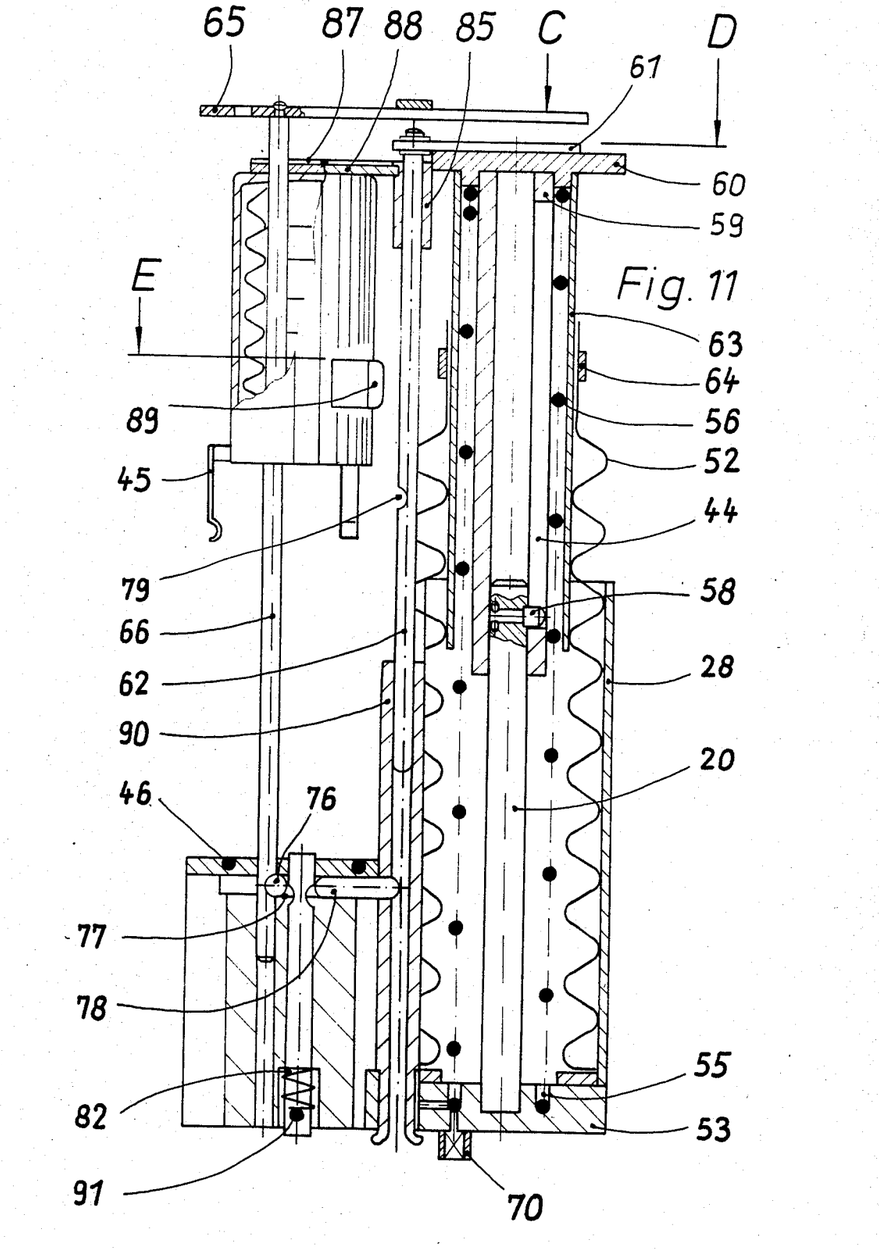
FIG. 11 shows a sectional side view of the device in FIG. 9. The suction producing folding bellows is extended and cut through the middie, while the tubular housing is cut in the rear (along the cut line A-B of FIG. 10) to show the steering elements.

In FIG. 11, the longitudinal section line S (see A-B in FIG. 10) goes on the right side at first through the middle of the central rod (57) but then in the rear through the rod (62) and the middle of the angular groove (72), whereby the positioning of the most important steering mechanisms becomes visible. The rod (62) is drawn by the action of the pressure spring (56) that distance out of the leading tube (90), which the length of the slit (44) in the tube (59) up to the stop of the cross-pin (58) permits. While the pressure spring (82) acts upon the cross-rod (91), it also lowers the releasing bar (75), so that the holding rod (78) is pushed to the right out of its annular groove (77). This was possible, because the rod (66) was raised, and, before that, the ball (76) could move into the notch of the blocking rod (66). The pot (48) is pulled up by hand, whereby the connecting bush (85) is pushed along the rod (62), until the spring baffle (86)—as can be clearly seen in the illustration—snaps into a notch in the rod (62). The pot (48) with the cross-plate (88), which itself is a part of the connecting bush (85) is attached above the leaf spring plate (87). The cross rail (89) on the pot—seen from above in the illustration13 facilitates the tipping of the pot to the left, until the cross bolt meets the blocking rods (66,67).

Figure 12:
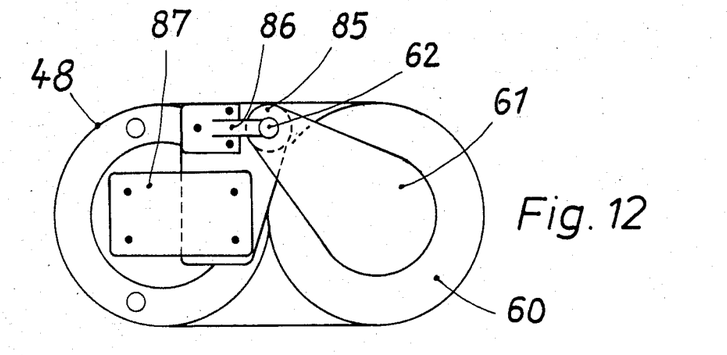
FIG. 12 is a view from above of the protective plate (65) on the level of view C of FIG. 11.

FIG. 12 shows a view from above on the level of D of FIG. 10 with the connection between the bush (85) and the pot (48) and the engagement of the leaf spring plate (86) in a notch of the rod (62).

Figure 13:
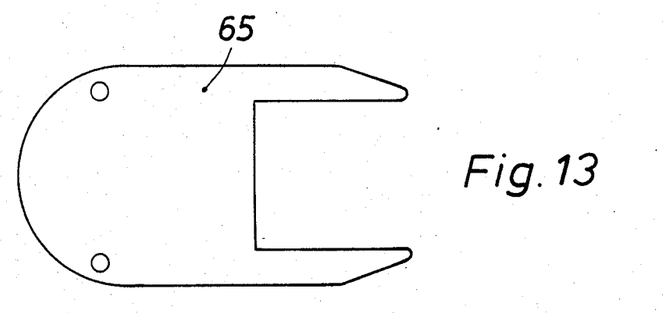
FIG. 13 is a view from above of the pot (48) in view D of FIG. 11.

FIG. 13 shows a view from above of the protective plate (65) on level C of FIG. 10.

Figure 14:
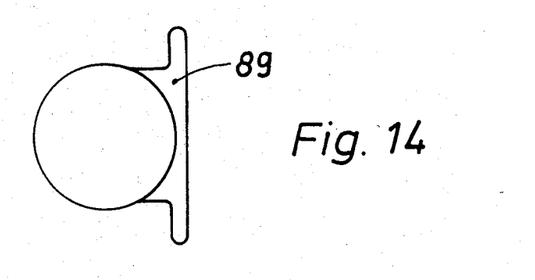
FIG. 14 is a view from above of the crossrail (89) in view E of FIG. 11.

FIG. 14 shows the cross rail (89) on the pot (48) seen from above.

To use the device, the blocking rods (66, 67) must be drawn up by pulling on the protective plate (65), so that the bias spring (82) can lift the releasing bar (75), for which the pushing of the ball (76) into the notch of the blocking rod (66) is a precondition. It is practical then to pull the pot up on the cross rail (89) along the rod (62), to snap out the pot (48) to the right while bending the leaf spring plate (87) out of its perpendicular position, to detach and remove any still present used syringes by turning the pot (48) and to put in the syringe, which has been prepared in the usual manner with the cannula attached, in such a way, that the syringe stamp reaches into the inside of the folding bellows, and the flange of the syringe cylinder penetrates through the oval hole in the lowest plate for attachment to the pot (48) and strikes against the round hole disc (see FIGS. 3 and 11). The flange is locked by being turned within the distance ring between the hole disc and the oval hole. If the pot (48) is released, it assumes with the syringe a perpendicular position under the influence of the leaf spring plate (87), which stretches out again. Now, after the resistance of the spring baffle (86) has been overcome, the pot (48) is lowered, until the three fixing brackets (45) snap into place over the baffles of the cover (42). Pressure through the forked continuations of the protective plate (38) on the connecting plate (65) causes a lowering of the sleeve (63) and of the tube (59) inside the folding bellows (52) and a pushing together of the bellows. Pressure must be put on the shell (36), which surrounds the suction cup, in order to bring about the lowering of the folding bellows (52) and of those parts which reach, over the rim of the protective tube (54). The releasing bar is thus raised, so that the catch pin (78) retreats under pressure of the rod (62) on its head onto the annular groove (77) of the releasing rod, so that the rod (62) can move by the latter. It is best, if the device is for this purpose pressed with the base plate (53) against the surface of a table in such a manner that the suction triggering shell (36) sticks up freely in the air. The air, which is pressed out of the folding bellows (52), excapes through the cross-over duct (68) into the area of the cannula attachment. By means of a downwards movement of the releasing bar (75), the catch pin (78) is now pressed into the notch (79) of the rod (62) thus limiting the upwards movement of the latter in conjuction with the taut pressure spring (56). If the shell (36) is now pressed in a crooked position on the skin, the unequal pressure on the parts of the ring causes those parts under more pressure to prevent by friction on the tubular housing (1) the gliding movement of the shell (36) and thus the triggering of suction.

If the shell (36) is properly positioned, the equally distributed pressure on its lower rim causes its upper rim to move the releasing bar (75) against the pressure springs (56, 82). The annular groove (77) frees the movement of the catch pin (78) to the left at that moment, in which the skin, rising because of pressure, moves past the outer rim of the suction cup. The rod (62) is released, and the partial vacuum, which has been created by the expnsion of the folding bellows (52) and of the space which is contained within the sleeve (63), causes suction through the cross-over duct (68) to effect, first, the skin, which has been enclosed by the rim of the suction cup, and raises the skin onto the point of the cannula and then moves past the syringe cylinder into the smaller folding bellows (50), which because of this contracts, thus, by means of pressure on the syringe stamp, bringing about the injection. Air comes gradually into the interior of the folding bellows (52) and the tubular housing (1) through the throttle-nozzle (70), whereby the skin pulls itself back again from the cannula.

The invention should, with regard to means of sealing the tubular housing against the exterior air, not limit itself to pistons of folding bellows but should rather include all membranes and sealing bodies, such as balls.

It will be understood that each of the elements described above, or two or more together may also find useful application in other types of suction injectors differing from the types described above.

While the invention has been illustrated and described as embodied in a suction injector, it is not intended to be limited to the details shown, since various modifications and structural changes may be made without departing in any way from the spirit of the present invention.

Without further analysis, the foregoing will so fully reveal the gist of the present invention that others can, by applying the current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims.

I claim:

1. A suction injector, particularly for use with hypodermic injections, comprising:
   a tubular housing;
   partitioning means, slidably disposed in the housing and frictionally sealed against the housing, thereby dividing the housing into two chambers of oppositely varying volume;
   supporting means in one of the chambers of the housing, on one side of said partitioning means, for supporting a container filled with medicine and constructed to be operated by volume reduction in said chamber and having a cannula for ejecting the medicine in the container;
   suction cup means at one end of the housing, being at the same side of said partitioning means as said supporting means;
   means for applying a vaccum to said one chamber at said same side of the partitioning means to be effective also at the suction cup, so that skin forced into the suction cup thereby being penetrated by the cannula; and
   due to said friction, said partitioning means delayedly sliding exclusively on account of the established vacuum in said one chamber towards the container for operating the same through reduction in volume of said chamber in order to obtain ejection of medicine through the cannula.

2. The injector of claim 1, wherein said sealing partitioning means is a piston.

3. The injector of claim 1, wherein said sealing partitioning means is a folding bellows.

4. The injector of claim 1, wherein said sealing partitioning means is a ball.

5. The injector of claim 2, wherein said supporting means is a case for the container being fastened on said piston.

6. The injector of claim 5, wherein said supporting means on the piston is comprised of springing clamps.

7. The injector of claim 5, wherein a spring biased plate is provided to operate the supporting means.

8. The injector of claim 1, wherein said suction cup is comprised of a socket connecting to the tubular housing.

9. The injector of claim 1, wherein said suction cup is comprised of a tube inserted inside of said tubular housing.

10. The injector of claim 1, wherein said container a syringe with a cannula with a tip.

11. The injector of claim 1, wherein said cannula is fixed with a bag on said supporting case.

12. The injector of claim 1, wherein said suction hose has a mouthpiece on one end.

13. The injector of claim 1, wherein there are two tubes, parallel in axis, one of which operates, when said tubular housing and said suction cup have sealed off a piston with a (bayonet) cap catch for a rod with a handle piece opposite to said suction cup, and the other of which is continuously connected to said suction hose and has a sealing lid, which operates, when said vacuum source is connected with said suction hose, and a (bayonet) cap catch for said rod with a handle piece opposite from said sealing lid, and wherein a valve is operated for air flow in said suction hose, in such a manner, that the underpressure produced by said sealing piston under said sealing lid and by said rod is stored, until said valve is opened by hand operation after the removal of said rod and the positioning of the suction cup on the skin, and the suction raises the skin into the canula and then moves said piston with said supporting case, so that said syringe is emptied under the skin.

14. The injector as in claim 13, wherein a blocking lever, which works against said suction producing piston, is provided to fasten said piston for storing suction or to release the fastening for reventilation.

15. The injector as in claim 1, wherein said vacuum is a folding bellows extended by a spring.

16. The injector as in claim 15, wherein said spring for the extension of said folding bellows is activated by the shifting movement of a biased shell surrounding said suction cup and provided with a movable inner biased ring on said tubular housing, which becomes blocked and fixed there by bolts in the openings, if the rim (of said openings) of said shell are exposed to uneven even pressure by crooked application of the skin.

17. The injector as in claim 15, wherein the said bolts, for the better limitation of movement, are positioned opposite from one another and positioned in round holes serving as openings.

18. The injector as in claim 15, wherein said tubular housing is sealed and covered by a folding bellows and surrounded by a tube, both of which include the syringe piston; said tubular housing being in connection with said suction producing folding bellows by means of a cross over duct; a rod is connected with the lid of said suction producing folding bellows with a notch for a holding rod working together with a notch of the 19. The injector as in claim 1, wherein said tube, surrounding said folding bellows, is fastened to said rod, which is connected with said lid of the suction producing folding bellows by a bush sliding on said rod.

20. The injector, as in claim 15, wherein a leaking nozzle is provided for the reventilation after the injection.

21. The injector, as in claim 20, wherein said nozzle is replaced by a membrane, which is semipermeable for gases.

22. The injector as in claim 15, wherein said suction producing folding bellows is connected in a sealed manner with a tube sliding on a rod inside of the folding bellows.

* * * * *